United States Patent [19]

Ratton et al.

[11] Patent Number: 4,885,408

[45] Date of Patent: Dec. 5, 1989

[54] CHLORINATION OF ORTHO-SUBSTITUTED PHENOLS

[75] Inventors: Serge Ratton, Villefontaine; Jean-Roger Desmurs, Saint-Symphorien d'Ozon, both of France

[73] Assignee: Rhone-Poulenc Chimie, Courbevoie, France

[21] Appl. No.: 69,233

[22] Filed: Jul. 2, 1987

[30] Foreign Application Priority Data

Jul. 2, 1986 [FR] France ................................ 86 09813

[51] Int. Cl.$^4$ .............................................. C07C 39/32
[52] U.S. Cl. .................................. 568/779; 568/774; 568/776
[58] Field of Search .................... 568/774, 776, 779

[56] References Cited

U.S. PATENT DOCUMENTS

| | | | |
|---|---|---|---|
| 4,237,321 | 12/1980 | Cutbertson | 568/776 |
| 4,564,714 | 1/1986 | Virgillo et al. | 568/776 |

FOREIGN PATENT DOCUMENTS

| | | | |
|---|---|---|---|
| 0196260 | 10/1986 | European Pat. Off. | 568/776 |
| 0216714 | 4/1987 | European Pat. Off. | 568/776 |
| 1157540 | 7/1969 | United Kingdom | 568/776 |
| 2135310 | 8/1984 | United Kingdom | 568/776 |
| 2177396 | 1/1987 | United Kingdom | 568/776 |

*Primary Examiner*—Werren B. Lone
*Attorney, Agent, or Firm*—Burns, Doane, Swecker & Mathis

[57] ABSTRACT

The ortho-substituted phenols, e.g., 2,6-dichlorophenol, are reacted with gaseous chlorine, in the presence of a catalytically effective amount of a strong or Lewis acid, to produce, e.g., a more pure 2,4,6-trichlorophenol in good yield.

21 Claims, No Drawings

CHLORINATION OF ORTHO-SUBSTITUTED PHENOLS

BACKGROUND OF THE INVENTION

1. Field of the Invention

The present invention relates to an improved process for the chlorination of phenolic compounds utilizing gaseous chlorine, which phenolic compound starting materials are substituted in both ortho positions with respect to the hydroxyl group.

2. Description of the Prior Art

Exemplary of an important phenolic compound which can be prepared by chlorination of an ortho-substituted phenolic compound is 2,4,6-trichlorophenol.

The usual process for the preparation of 2,4,6-trichlorophenol comprises the chlorination of 2,4-dichlorophenol.

However, a minor proportion of 2,4,5-trichlorophenol (on the order of 0.003 to 0.0010% of the weight of 2,4,6-trichlorophenol) is concomitantly formed. 2,4,6-Trichlorophenol, which is an intermediate in the synthesis of various other compounds, should be as pure as possible and should not contain any trace amounts of the 2,4,5-isomer.

One solution to this problem, therefore, would be to chlorinate 2,6-dichlorophenol, which would completely avoid the formation of 2,4,5-trichlorophenol. 2,3,6-Trichlorophenol, which can form in trace amounts in this particular instance, is far less problematical than 2,4,5-trichlorophenol.

Indeed, when 2,6-dichlorophenol is chlorinated with gaseous chlorine, it is found that the yield obtained is not particularly attractive. More specifically, a considerable amount of 2,4,5,6,6-pentachloro-2-cyclohexenone is formed, and this makes the reaction mixture highly unstable and difficult to purify.

SUMMARY OF THE INVENTION

Accordingly, a major object of the present invention is the provision of an improved $Cl_2$ chlorination process which is conspicuously devoid of those drawbacks and disadvantages to date characterizing the state of this art.

Another object of this invention is the provision of an improved para-chlorination process, in general, whereby the ortho-substituted phenols are para-chlorinated in attractive yields.

Briefly, the present invention features the chlorination, with gaseous chlorine, of phenolic compounds having the general formula (1):

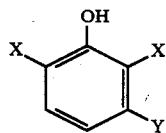

(1)

in which the symbols X, which may be identical or different, are each a chlorine atom, a bromine atom, a methyl or ethyl group, a methoxy or ethoxy group, or an acetoxy group, the symbol Y represents a hydrogen atom, a methyl or ethyl group, or a methoxy or ethoxy group; and wherein the reaction is carried out in the presence of a catalytically effective amount of a strong acid or a Lewis acid.

DETAILED DESCRIPTION OF THE PREFERRED EMBODIMENTS OF THE INVENTION

More particularly according to the present invention, by the term "strong acid" is intended a protonic acid which has an acidity function Ho less than or equal to $-5$.

As specific examples of such strong acids, representative are, without limitation: sulfuric acid, perchloric acid, trifluoromethanesulfonic acid, chlorosulfonic acid, fluorosulfonic acid, pyrosulfuric acid and acidic resins containing fluorosulfonic groups.

By the term "Lewis acid" is intended its art-recognized definition, i.e., compounds which are acceptors of electron pairs. In particular, the Lewis acids noted in the text edited by G. A. Olah, *Friedel-Crafts and Related Reactions*, volume 1, pages 191 to 197 (1963) are representative.

The Lewis acids which are advantageously used in the process of the invention are, more particularly, the halides of the elements of Groups 3a, 4a, 5a, 1b, 2b, 4b, 5b, 6b, 7b and 8 of the Periodic Table which are liquid or solid under the reaction conditions, such as aluminum, tin, phosphorus, antimony, arsenic, bismuth, titanium, tantalum, niobium, zirconium, vanadium, tungsten, molybdenum, iron, cobalt, nickel, copper, zinc and cadmium chlorides, bromides, fluorides and iodides.

As specific examples of such halides, representative are aluminum chloride, aluminum bromide, stannic and stannous chlorides, stannic and stannous bromides, bismuth trichloride, titanium tetrachloride, zirconium tetrachloride, antimony pentafluoride, tungsten hexachloride, molybdenum chlorides, ferric chloride, ferrous chloride, ferric bromide, ferrous bromide, cuprous chloride, cupric chloride and zinc chloride.

Among these Lewis acids, aluminum chloride, ferric chloride, zirconium tetrachloride and titanium tetrachloride are the preferred.

It is also possible to use complexes of certain Lewis acids with a hydrogen acid, insofar as these complexes are liquid or solid under the reaction conditions. Thus, for example, the complex $SbF_5 \cdot HF$ can be used.

In general, the amount of strong acid or Lewis acid which is employed is such that the weight ratio of the strong acid to the phenolic compound of formula (1) or of the Lewis acid to the phenolic compound of formula (1) ranges from 0.01% to 10%.

Preferably, these weight ratios range from 0.1% to 5%.

The process according to the invention may be carried out in the absence of solvent, namely, when the reactants are in the molten state.

In the molten state, it is more particularly preferred to use a strong protonic acid such as defined above.

For example, 2,4,6-trichlorophenol is thus prepared in excellent yield, typically containing less than 3% by weight of 2,4,5,6,6-pentachloro-2-cyclohexenone.

It is also possible to utilize a liquid medium of a carboxylic acid such as acetic acid, a chloroacetic acid, a fluoroacetic acid, or propionic acid.

When a liquid medium is employed to carry out the process of the invention, in most cases it is acetic acid or trifluoroacetic acid.

In a liquid medium, very good results are obtained using a strong protonic acid just as well as with a Lewis acid, such as those defined above.

For example, in the case of the chlorination of 2,6-dichlorophenol, the yields of 2,4,6-trichlorophenol, typically containing less than 3% by weight of 2,4,5,6,6-pentachloro-2-cyclohexenone, are excellent.

The quantity of chlorine which is employed in the process of the invention is essentially a function of the required degree of conversion of the phenolic compound (1).

In practice, in most cases the chlorine gas is introduced into the reaction mixture by sparging. The pressure in the apparatus is therefore substantially equal to or slightly higher than atmospheric pressure.

The chlorine may be employed by itself, or may be diluted with an inert gas such as, for example, nitrogen. The presence of an inert gas makes it possible, if need be, to increase the gas flow without a proportional increase in the quantity of chlorine introduced over a given time period.

The gaseous chlorine employed in the present process may also be produced in situ, from hydrochloric acid, by the addition of an oxidizing compound such as, for example, hydrogen peroxide.

The temperature at which the process of the invention is carried out is typically less than or equal to 180° C. The lower limit is not critical. It is determined by the requirement that the reaction mixture be liquid.

When the operation is carried out in the molten state, this lower temperature will therefore vary depending on the phenolic compound (1) subjected to chlorination. Thus, when 2,6-dichlorophenol is being chlorinated, a temperature of at least 65° C. will be required.

When the operation is carried out in a carboxylic acid medium, it is possible to utilize a temperature as low as, for example, 20° C.

Preferably, however, the temperature will range from 40° C. to 120° C., when a carboxylic acid medium is present.

When the operation is carried out in the molten state, the preferred temperatures will also range from 40° C. to 120° C., except, of course, in the case of the phenolic compounds having a melting point above 40° C., for which the preferred temperature will range from their melting points to 120° C.

Exemplary of the phenolic compounds of formula (1) to which the process of the invention is applicable, particularly representative are: 2,6-dichlorophenol, 2,6-dimethoxyphenol, 2-chloro-6-methoxyphenol, 2-chloro-6-methylphenol, 2,6-dichloro-3-methylphenol, 2,6-dichloro-3methoxyphenol and 2-bromo-6-methoxyphenol.

It is possible, if desired, to chlorinate mixtures of these phenolic compounds.

As above indicated, the process of the invention is most particularly adapted for the chlorination of 2,6-dichlorophenol to produce 2,4,6-trichlorophenol, since it enables the latter compound to be facilely prepared, while at the same time very greatly limiting the formation of unwanted secondary products such as 2,4,5,6,6-pentachloro-2-cyclohexenone.

In order to further illustrate the present invention and the advantages thereof, the following specific examples are given, it being understood that same are intended only as illustrative and in nowise limitative.

EXAMPLE 1

The following materials were introduced into a 100-cm$^3$ glass reactor equipped with a stirrer, a chlorine gas inlet tube and a thermometer, and supporting a condenser:

(i) 2,6-dichlorophenol: 32.6 g (0.2 mole);
(ii) trifluoromethane sulfonic acid: 0.16 g (1.07 $10^{-3}$ mole).

The temperature of the reaction mixture was raised to 70° C. and the addition of gaseous chlorine, at a flow rate of 5 liters/hour, was commenced, the stirring being continued. The chlorination time was 54 minutes, which corresponded to 4.48 liters of added chlorine (0.2 mole).

Upon completion of the reaction, the entire apparatus was purged with a stream of nitrogen.

The final reaction mixture was colorless in melt form; it was white/very pale yellow in solid form and weighed 38.42 g.

The reaction mixture was analyzed by gas phase chromatography (GPC) and by high pressure liquid phase chromatography (HPLPC). The following results were obtained:

(a) Degree of conversion (DC) of 2,6-dichlorophenol: 83.5%
(b) Yield (Y) of 2,4,6-dichlorophenol, based on the 2,6-dichlorophenol converted: 99.8%.

Furthermore, the following were noted:
(c) The absence of pentachlorocyclohexenone;
(d) The presence of a small amount of polychlorophenoxyphenol: Y=0.07%.

EXAMPLE 2

The procedure was the same as in Example 1.
The following materials were charged:
(i) 2,6-dichlorophenol: 65.2 g (0.4 mole);
(ii) trifluoromethanesulfonic acid: 0.33 g (2.15 $10^{-3}$ mole).

The chlorination was carried out at 70° C. with a chlorine flow rate of 5 liters/hour. In order to convert virtually all of the 2,6-dichlorophenol, the amount of chlorine introduced was 0.5 mole of chlorine.

The resulting reaction mixture was very slightly yellow in the molten state and practically white in the solid state.

It weighed 79.50 g.
The following results were obtained:
(a) DC of 2,6-dichlorophenol: 99.8%
(b) Y of 2,4,6-trichlorophenol: 96.0%
(c) Y of 2,3,4,6-tetrachlorophenol: 1.5%.

Furthermore, the following were observed:
(d) The absence of pentachlorocyclohexenone;
(e) The absence of polychlorophenoxyphenols.

EXAMPLE 3

The procedure was the same as in Example 1.
The following materials were charged:
(i) 2,6-dichlorophenol: 32.6 g (0.2 mole);
(ii) 95% sulfuric acid: 0.33 g.

The chlorination was carried out at 70° C. with a chlorine flow rate of 5 liters/hour. The amount of chlorine introduced was 4.48 liters (0.2 mole).

The following results were obtained:
(a) DC of 2,6-dichlorophenol: 77.6%
(b) Y of 2,4,6-trichlorophenol: 97.0%
(c) Y of 2,3,4,6-tetrachlorophenol: 0.3%
(d) Y of pentachlorocyclohexenone: 2.4%.

EXAMPLE 4

The procedure was the same as in Example 1.

The following materials were charged:
(i) 2,6-dichlorophenol: 32.6 g (0.2 mole);
(ii) 70% perchloric acid: 0.33 g.

The chlorination was carried out at 70° C. with a chlorine flow rate of 5 liters/hour. The amount of chlorine introduced was 4.48 liters (0.2 mole).

The following results were obtained:
(a) DC of 2,6-dichlorophenol: 84.8%
(b) Y of 2,4,6-trichlorophenol: 99.0%
(c) Y of 2,3,4,6-tetrachlorophenol: 0.3%
(d) Y of pentachlorocyclohexenone: 1.0%.

EXAMPLE 5

This example illustrates the chlorination of 2,6-dichlorophenol into 2,4,6-trichlorophenol, in an acetic acid medium.

The procedure was the same as in Example 1, but a 250-cm³ glass reactor was employed.

The following materials were charged:
(i) 2,6-dichlorophenol: 32.6 g (0.2 mole);
(ii) acetic acid: 100 cm³;
(iii) trifluoromethanesulfonic acid: 0.16 g.

The chlorination was carried out at 70° C. with a chlorine flow rate of 5 liters/hour. The amount of chlorine introduced was 4.48 liters (0.2 mole).

The following results were obtained:
(a) DC of 2,6-dichlorophenol: 90.0%
(b) Y of 2,4,6-trichlorophenol: 99.8%.

No trace amounts of pentachlorocyclohexenone or of polychlorophenoxyphenols were detected.

EXAMPLES 6 TO 8

The procedure was the same as in Example 1.

The following materials were charged:
(i) 2,6-dichlorophenol: 32.6 g (0.2 mole);
(ii) strong protonic acid: see Table I;
(iii) chlorine (flow rate 5 liters/hour): 0.2 mole.
Reaction temperature: 70° C.
Chlorination time: 54 minutes.

Table I below reports the nature and the quantity of the catalyst employed, as well as the DC of 2,6-dichlorophenol (DCP) and the Ys of 2,4,6-trichlorophenol (TCP) and, where applicable, of pentachlorocyclohexenone (PCCH), polychlorophenoxyphenol (PCPP) and 2,3,4,6-tetrachlorophenol (TTCP).

EXAMPLES 9 AND 10

The procedure was the same as in Example 5.

The following materials were charged:
(i) 2,6-dichlorophenol: 32.6 g (0.2 mole);
(ii) Lewis acid: see Table II;
(iii) acetic acid: 100 cm³;
(iv) chlorine (flow rate 5 liters/hour): 0.2 mole.
Reaction temperature: 70° C.
Chlorination time: 54 minutes.

Table II below reports the nature and the amount of the catalyst employed, together with the DC of 2,6-dichlorophenol (DCP) and the Ys of 2,4,6-trichlorophenol (TCP) and, where applicable, of pentachlorocyclohexenone (PCCH), polychlorophenoxyphenol (PCPP) and 2,3,4,6-tetrachlorophenol (TTCP).

EXAMPLES 11 AND 12

The procedure was the same as in Example 1.

The following materials were charged:
(i) 2,6-dichlorophenol: 32.6 g (0.2 mole);
(ii) Lewis acid: see Table III;
(iii) chlorine (flow rate 5 liters/hour): 0.2 mole.
Reaction temperature: 70° C.
Chlorination time: 54 minutes.

Table III below reports the nature and the amount of the catalyst employed, together with the DC of 2,6-dichlorophenol (DCP) and the Ys of 2,4,6-trichlorophenol (TCP) and, where applicable, of pentachlorocyclohexenone (PCCH), polychlorophenoxyphenol (PCPP) and 2,3,4,6-tetrachlorophenol (TTCP).

TABLE I

| TESTS | CATALYST Nature | CATALYST Quantity | DC of DCP | Y of TCP | Y of PCCH | Y of PCPP | Y of TTCP |
|---|---|---|---|---|---|---|---|
| Control | none | — | 66.1% | 76.2% | 16.9% | — | — |
| Example 6 | H$_2$SO$_4$ | 1.63 g | 73.3% | 99.0% | 0.5% | — | 0.5% |
| Example 7 | CF$_3$SO$_3$H | 0.33 g | 81.6% | 98.8% | 0.4% | — | 9.5% |
| Example 8 | H$_2$SO$_4$ | 0.01 g | 62.5% | 86.2% | 11.2% | — | 1.3% |

TABLE II

| TESTS | CATALYST Nature | CATALYST Quantity | DC of DCP | Y of TCP | Y of PCCH | Y of PCPP | Y of TTCP |
|---|---|---|---|---|---|---|---|
| Example 9 | AlCl$_3$ | 0.33 g | 90.8% | 99.5% | — | 0.4% | — |
| Example 10 | FeCl$_3$ | 0.33 g | 84.2% | 99.1% | — | — | 0.7% |

TABLE III

| TESTS | CATALYST Nature | CATALYST Quantity | DC of DCP | Y of TCP | Y of PCCH | Y of PCPP | Y of TTCP |
|---|---|---|---|---|---|---|---|
| Example 11 | AlCl$_3$ | 0.33 g | 93.4% | 83.3% | — | 0.8% | 14.2% |
| Example 12 | FeCl$_3$ | 0.33 g | 89.4% | 80.3% | — | 0.5% | 17.8% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the chlorination of orthosubstituted phenols, comprising reacting gaseous chlorine with a phenolic compound having the general formula (1):

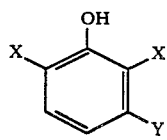

wherein each X, which may be identical or different, is a chlorine or bromine atom, a methyl or ethyl group, a methoxy or ethoxy group, or an acetoxy group, and Y is a hydrogen atom, a methyl or ethyl group, or a methoxy or ethoxy group, in the presence of a catalytically effective amount of a strong acid or Lewis acid.

2. The process as defined by claim 1, carried out in the presence of a catalytically effective amount of a protonic acid having an acidity function Ho less than or equal to −5.

3. The process as defined by claim 1, said protonic acid comprising sulfuric acid, perchloric acid, trifluoromethanesulfonic acid, chlorosulfonic acid, fluorosulfonic acid, pyrosulfuric acid or an acidic resin containing fluorosulfonic groups.

4. The process as defined by claim 1, carried out in the presence of a catalytically effective amount of a Lewis acid.

5. The process as defined by claim 4, said Lewis acid comprising a chloride, bromide, fluoride or iodide of aluminum, tin, phosphorus, antimony, arsenic, bismuth, titanium, tantalum, niobium, zirconium, vanadium, tungsten, molybdenum, iron, cobalt, nickel, copper, zinc or cadmium, or a complex of a Lewis acid with a hydracid.

6. The process as defined by claim 5, said Lewis acid comprising aluminum chloride, aluminum bromide, stannic or stannous chloride, stannic or stannous bromide, bismuth trichloride, titanium tetrachloride, zirconium tetrachloride, antimony pentafluoride, tungsten hexachloride, a molybdenum chloride, ferric chloride, ferrous chloride, ferric bromide, ferrous bromide, cuprous chloride, cupric chloride or zinc chloride.

7. The process as defined by claim 6, said Lewis acid comprising aluminum chloride, ferric chloride, zirconium tetrachloride or titanium tetrachloride.

8. The process as defined by claim 1, wherein the weight ratio of the strong or Lewis acid to the phenolic compound (1) ranges from 0.01% to 10%.

9. The process as defined by claim 8, said weight ratio ranging from 0.1% to 5%.

10. The process as defined by claim 1, carried out in a liquid medium comprising a carboxylic acid.

11. The process as defined by claim 10, said carboxylic acid comprising acetic acid, a chloroacetic acid, a fluoroacetic acid, or propionic acid.

12. The process as defined by claim 1, carried out at a temperature ranging from the melting point of the phenolic compound (1) to 180° C.

13. The process as defined by claim 1, carried out at a temperature ranging from the melting point of the phenolic compound (1) to 120° C.

14. The process as defined by claim 1, carried out in the molten state.

15. The process as defined by claim 1, carried out at a temperature ranging from 20° to 180° C.

16. The process as defined by claim 15, said temperature ranging from 40° to 120° C.

17. The process as defined by claim 1, said phenolic compound (1) comprising 2,6-dichlorophenol, 2,6-dimethoxyphenol, 2-chloro-6-methoxyphenol, 2-chloro-6methylphenyl, 2,6-dichloro-3-methylphenol, 2,6-dichloro-3-methoxyphenol or 2-bromo-6-methoxyphenol.

18. The process as defined by claim 17, said phenolic compound (1) comprising 2,6-dichlorophenol.

19. The process as defined by claim 1, for the preparation of 2,4,6-trichlorophenol.

20. The process as defined by claim 1, wherein the gaseous chlorine is produced in situ.

21. The process as defined by claim 1, comprising diluting the gaseous chlorine with an inert gas.

* * * * *